US007476698B2

(12) United States Patent
Wagener et al.

(10) Patent No.: US 7,476,698 B2
(45) Date of Patent: *Jan. 13, 2009

(54) ANTIMICROBIAL ADHESIVE AND COATING SUBSTANCE AND METHOD FOR THE PRODUCTION THEREOF

(75) Inventors: Michael Wagener, Bremen (DE); Andreas Hartwig, Ritterhude (DE)

(73) Assignee: Bio-Gate AG, Nuremburg (DE)

( * ) Notice: Subject to any disclaimer, the term of this patent is extended or adjusted under 35 U.S.C. 154(b) by 431 days.

This patent is subject to a terminal disclaimer.

(21) Appl. No.: 10/489,891

(22) PCT Filed: Sep. 18, 2002

(86) PCT No.: PCT/EP02/10463

§ 371 (c)(1),
(2), (4) Date: Oct. 8, 2004

(87) PCT Pub. No.: WO03/024494

PCT Pub. Date: Mar. 27, 2003

(65) Prior Publication Data

US 2005/0080157 A1 Apr. 14, 2005

(30) Foreign Application Priority Data

Sep. 18, 2001 (DE) ................. 101 46 050

(51) Int. Cl.
*C09D 5/16* (2006.01)
(52) U.S. Cl. .................. 523/122; 524/403; 524/555; 524/560; 524/561; 524/562; 524/588; 524/589; 524/612
(58) Field of Classification Search ................. 523/122; 424/422; 524/403, 555, 560, 561, 562, 588, 524/589, 612
See application file for complete search history.

(56) References Cited

U.S. PATENT DOCUMENTS

| 4,849,223 | A |   | 7/1989  | Pratt et al.    |         |
|-----------|---|---|---------|-----------------|---------|
| 5,356,629 | A | * | 10/1994 | Sander et al.   | 424/422 |
| 5,595,750 | A | * | 1/1997  | Jacobson et al. | 424/421 |
| 5,837,275 | A |   | 11/1998 | Burrell et al.  |         |
| 5,985,308 | A | * | 11/1999 | Burrell et al.  | 424/426 |
| 6,124,374 | A |   | 9/2000  | Kolias et al.   |         |
| 6,216,699 | B1|   | 4/2001  | Cox et al.      |         |
| 6,303,183 | B1| * | 10/2001 | Wilczynski et al.| 427/193|
| 6,544,536 | B1| * | 4/2003  | Krall et al.    | 424/402 |
| 6,939,568 | B2| * | 9/2005  | Burrell et al.  | 424/618 |
| 6,984,392 | B2| * | 1/2006  | Bechert et al.  | 424/422 |
| 2005/0165372 | A1 | * | 7/2005 | Bechert et al. | 604/367 |
| 2007/0077312 | A1 | * | 4/2007 | Berchert et al.| 424/618 |
| 2007/0081958 | A1 | * | 4/2007 | Bechert et al. | 424/70.1 |
| 2007/0203442 | A1 | * | 8/2007 | Bechert et al. | 602/52 |

FOREIGN PATENT DOCUMENTS

| DE | 31 10 681 A1 | 9/1982 |
| DE | 32 28 849 A1 | 2/1984 |
| DE | 197 56 790 A | 7/1999 |
| DE | 197 56 790 A1 | 7/1999 |
| DE | 197 51 581 A1 | 8/1999 |
| DE | 199 58 458 A1 | 6/2001 |
| EP | 0 190 504 B1 | 4/1993 |
| WO | WO 81/02667 | 10/1981 |
| WO | WO 82/01990 | 6/1982 |
| WO | WO 84/01721 | 5/1984 |
| WO | WO 95/20878 | 8/1995 |

OTHER PUBLICATIONS

Raad I. et al., *J. Infec. Dis.* 173 (1996) pp. 495-498.
S. Nakano, T. Endo, *J. Polm. Sci.: Part A*, 34 (1996), pp. 475-480.
Bechert, Thorsten et al., *Nature Medicine*, vol. 6, No. 8 (Sep. 2000) pp. 1053-1056.
Database WPI, Section Ch, Week 199909, Derwent Publications Ltd., London, GB; Class A82 AN 1999-101274, XP002226346 & JP 10 330654 A (Sumitomo Cement Co Ltd), Dec. 15, 1998 Zusammenfassung.
Database WPI, Section Ch, Week 200171, Derwent Publications Ltd., London, GB; Class A96, AN 2001-613102, XP002226347 & JP 2001 137279 A (Sekisui Chem Ind Co Ltd), May 22, 2001 Zusammenfassung.
Bernd H. Gunther: "Metal Nanopowders for Electrically Conductive Polymers", The International Journal of Powder Metallurgy, vol. 35, No. 7, 1999, pp. 53-58.
Mehmet Turker, "Effect of Oxygen Content on the Sintering Behaviour of Silver Nanopowders Produced by Inert Gas Condensation", Turkish J. Eng. Env. Sci, 26 (2002), pp. 285-291, Gazi University, Technical Education Faculty, Metallurgy Department, Besevler, Ankara, Turkey.

* cited by examiner

*Primary Examiner*—Bernard Lipman
(74) *Attorney, Agent, or Firm*—Pearne & Gordon LLP

(57) ABSTRACT

The invention relates to an antimicrobial adhesive and coating material which contains as the antimicrobial component metallic silver particles with a content of less than 5 ppm of silver, sodium and potassium ions.

39 Claims, 3 Drawing Sheets

Figure 3:
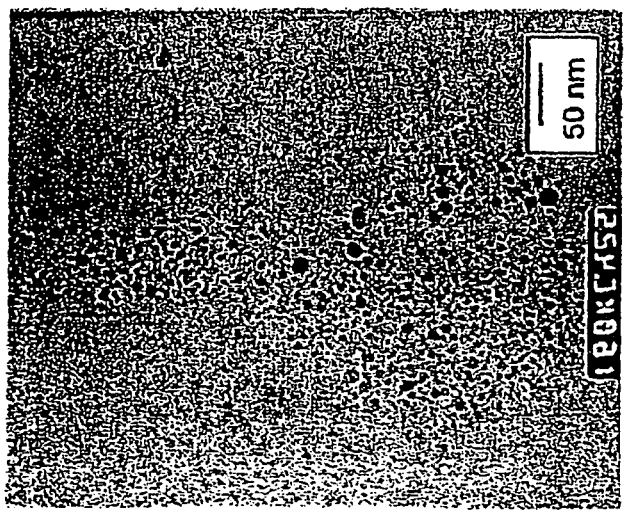

ANTIMICROBIAL ADHESIVE AND COATING SUBSTANCE AND METHOD FOR THE PRODUCTION THEREOF

The invention relates to an antimicrobial adhesive and coating material, a use of the adhesive and coating material and a method of manufacturing same.

The invention relates to the area of adhesive and coating materials for, in the broadest sense, medical, technical-medical or technical-hygienic applications. Antimicrobial adhesive and coating materials are used in particular for manufacturing plaster bandages, wound coverings, catheters, hygienic packaging materials, for coating the aforementioned materials as well as for coating components of technical medical devices and walls of rooms which must kept hygienic and similar. The use of such adhesive and coating materials is intended to prevent the invasion of micro-organisms.

From DE 199 58 458 A1 an antimicrobial wound covering is known. The wound covering is made of a synthetic polymer material containing zeolites containing metal-ions.

U.S. Pat. No. 6,124,374 describes an antimicrobial adhesive cream for dentures. The antimicrobial active substance used here are 2-valence copper salts.

From U.S. Pat. No. 6,216,699 B1 a pressure-sensitive adhesive substance is know to which diidomethyl-p-tolylsulfon is added as antimicrobial active substance.

The known antimicrobial constituents are not particularly universal. They are specifically adjusted to the particular matrix. The antimicrobial effectiveness of the thus mixed materials does not last particularly long.

From WO 95/20878 a method is known for manufacturing bactericidal or fungicidal plastic bodies. For this a thin layer of silver is first applied to a membrane film using thin-film technology. The membrane film is then broken up. The broken up membrane film is fused on and then put into the desired shape with conventional techniques.—The method is very time-consuming and expensive. It requires the manufacturing of a special intermediate product and its breakup.

From EP 0 190 504 an antimicrobial composition is known which contains 5 to 10 weight % of silver. To improve the antimicrobial properties a hydratable or a hydrated oxide is additionally added.

DE 31 10 681 C2 describes a material for bone implants. The material is made from a polymer to which silver phosphate is added as antimicrobial active substance.

From WO 81/02667 an antimicrobial surgical implant is known. Metallic silver is added to the implant as antimicrobial active substance.

WO 82/01990 of this type describes a bone cement based on polymethylmethacrylat as the main component to which 5 vol. % of a silver salt is added as antimicrobial active substance.

U.S. Pat. No. 5,837,275 discloses an antimicrobial material which contains, among others, silver particles with a grain size of less than 200 nm. The silver lattice has artificially-created lattice imperfections and flaws to facilitate the release of silver ions.

From WO 84/01721 a material containing silver sulfate or silver acetate is known. Within 24 hours this material releases a concentration of more than 1 μM of silver ions in a surrounding liquid.

DE 32 288 849 A1 describes a material with a coating of silver. Elementary carbon or titanium is added to the material. The addition is intended to facilitate an increased release of silver ions to the surroundings.

U.S. Pat. No. 4,849,233 discloses a bone cement to which approximately 10 weight % elementary silver is added as well as titanium oxide or tantal oxide. The bone cement is characterized by its high rate of release of silver ions.

The antimicrobial effectiveness of the materials known in accordance with the state of the art has been proven with the so-called inhibition zone measurement. The inhibition zone measurement is described, for example, in Raad I. et al., J. Infec. Dis. 173 (1996). For this the material to be tested is placed in a culture medium such as Agar. Due to the release of antimicrobial acting metallic ions an inhibition zone forms around the material. The formation and the size of such an inhibition zone has been evaluated in accordance with the state of the art as the indication of the antimicrobial effectiveness of the material.

The materials known in accordance with the state of the art have the disadvantage that they initially release an excessive concentration of silver ions. According to more recent findings, materials which show an inhibition zone are not suitable for use in medical applications. Such materials release silver ions in macroscopic visible amounts to the surrounding tissue. Such amounts of silver ions are cytotoxic however. To the extent that such materials are approved at all by certifying authorities, approval is meanwhile now only given in accordance with pharmaceutical law. Such an approval is extremely expensive and time-consuming.

Seen as a whole no antimicrobial adhesive and coating material in accordance with the state of the art is yet known that does not indicate an inhibition zone with the inhibition zone test and is thus not cytotoxic.

Object of the invention is to remove the disadvantages in accordance with the state of the art. In particular an adhesive and coating material that can be manufactured as simply and inexpensively as possible is to be specified which is not cytotoxic and whose antimicrobial effectiveness lasts as long as possible. As defined in a further goal of the invention the adhesive and coating material is to be designed for as universal use as possible and permit the manufacture of thin coatings. Furthermore a simple and inexpensive method of manufacturing the adhesive and coating material is to be specified.

According to the invention an antimicrobial adhesive and coating material is suggested which contains metallic silver particles as antimicrobial component with a content of less than 5 ppm of silver, sodium and potassium ions. The suggested adhesive and coating material demonstrates an antimicrobial effectiveness of particularly long duration. It is not cytotoxic. In other words no inhibition zone can be observed during the inhibition zone test. This is attributed to the continuous low rate of silver ions released by the silver particles and diffused to the surface of the adhesive and coating material. According to the present state of knowledge, the low rate of release is attributed to the particularly low content of silver, sodium and potassium ions which is in total less than 5 ppm. The materials known in accordance with the state of the art primarily contain silver particles which initially release a high rate of silver ions. A high rate of release of silver ions is achieved, for example, with a disturbed lattice construction of the silver particles or with a high content of ions in the silver particles. Precisely this is not present in accordance with the subject of this invention.

The term adhesive and coating material means primarily and generally a synthetically manufactured material with an organic basis. In general the material hardens after processing. This can be a paint substance, a lacquer, an adhesive, in particular also with a thermoset or thermoplastic basis.

In accordance with a first embodiment the average grain size of the particles is less than 100 nm, preferably in the range of 5 to 50 nm. Such silver particles are suitable for the manufacture of nano-dispersed antimicrobial adhesive and coating materials.

In accordance with a further embodiment the silver particles are made of aggregates of primary particles with an average grain size of between 10 and 150 nm. Such silver particles are suitable for the manufacture of so-called nano-porous antimicrobial adhesive and coating materials.

In accordance with an advantageous embodiment the primary particles have an average grain size in the range of 80 to 140 nm. Silver particles created from such primary particles demonstrate a particularly good antimicrobial effectiveness. They are not cytotoxic.

In accordance with an advantageous embodiment the aggregates have an average grain size of 1 to 20 µm, preferably 10 to 20 µm. It has shown to be useful that the surface of the aggregates is 3 to 6 $m^2/g$. They can have a porosity of up to 95%. A porosity of between 70 and 95% has been shown to be useful. The aforementioned features contribute to a uniform and cytotoxically harmless release of silver ions on the surface of the material.

It has been shown to be useful that the antimicrobial adhesive and coating material is manufactured from at least one liquid organic component. This can be hardened like lacquer or a paint color by evaporating a solvent. However it is also possible to polymerize the organic component for hardening, for example, via UV light, heat or other physical influences. The antimicrobial adhesive and coating material can also be manufactured by mixing the organic component with at least one additional liquid organic component. The additional organic component can be, for example, a hardener which causes polymerization. The silver particles can be added immediately to the liquid organic component or also immediately to a liquid precursor product of same. This makes it particularly simple to manufacture a particularly homogenous dispersion of silver particles. In particular, it is thus not necessary to make an intermediate product with a related great expense and amount of time and then to process this further.

In accordance with a further embodiment 0.01 to 5.0 weight % of silver particles can be added. Preferably 0.01 to 2.0 weight % are added. The silver particles used by the invention have an antimicrobial effect over a long period already in a low concentration without causing a cytotoxic effect. It has been shown to be useful that the particles are spherical, in particular ball-shaped. This simplifies the mixing of silver particles into the liquid organic component. A homogenous dispersion can be made quickly. It is advantageous that the aggregates are completely infiltrated with the organic component.

The organic component and/or the additional organic component can contain an acrylate or a methacrylate as an essential constituent. Furthermore they can contain an epoxide, urethane, silicone or cyanoacrylate as an essential constituent.

In a further embodiment the antimicrobial adhesive and coating material contains as further addition cations of at least one of the following metals: Au, Pt, Pd, Ir, Sn, Cu, Sb, Zn. The further addition increases and/or lengthens the period of antimicrobial effectiveness. It has shown to be useful that the cations are bound in ion exchangers, added in the form of a complex or as a salt. The cations can diffuse from the adhesive and coating material to their surface and develop their antimicrobial effectiveness there. In this connection it has been shown to be useful that the salt of a, preferably polymeric, carboxylic acid is used as the salt.

The adhesive can be a pressure-sensitive adhesive. The organic and/or the further organic component can contain one or more of the following constituents: solvent, filler material, pigment, binding agent, plasticizer, drying accelerator, fungicide. The coating material can be a lacquer, a paint substance or a dispersion which can be hardened.

In further accordance with the invention a use of the adhesive and coating material provided by the invention is provided for the manufacture and/or coating of wound coverings, bandages, incontinence products, diapers for example, medical devices, packaging materials, for the coating of walls of buildings, housings and/or components of technical devices. For instance the interior walls of the housing of air-conditioners, the walls of operating rooms, containers for the production and storage of perishable foodstuffs, packaging material for disposable medical devices, disposable medical devices, bandages, medical instruments, etc. can be coated with the material provided by the invention or made thereof.

In further accordance with the invention a method for the manufacture of the adhesive and coating material according to the invention is provided with the following steps:

generation of a silver vapor by sputtering or by vaporization in a vacuum recipient, condensation of the silver vapor so that silver particles are formed with a content of less than 5 ppm of silver, sodium and potassium ions, mixing of the silver particles with a liquid organic component and at least partially hardening of the organic component.

The suggested method is simple and inexpensive to execute.

It can be used to make an antimicrobial adhesive and coating material whose antimicrobial effectiveness lasts for a particularly long period and, at the same time, has no cytotoxic effect on tissue which is in contact with it. The method can be used to make solid adhesive and coating materials and partially hardened pressure-sensitive adhesives. The method is generally also suitable for the manufacture of plastics, preferably made of at least one liquid component. For example medical devices such as catheters and similar can be made from such plastics.

With a first version of the method the silver vapor is condensed during the vapor phase so that aggregates are created from primary particles with an average grain size of 10 to 150 nm which aggregates have an average grain size of 1 to 20 µm.

With this version of the method the primary particles are created from the vapor phase. The created primary particles have an extremely high surface energy. When primary particles aggregate to each other the present activation energy already causes diffusion processes which cause the formation of sinter necks. Aggregates are formed in which the primary particles are connected with each other by sinter necks. Highly porous aggregates can be created in this way.

In accordance with a further version of the method the silver vapor is condensed on the surface of a liquid so that the silver particles have an average grain size of between 10 and 100 nm. With this version of the method the formation of agglomerates is prevented by withdrawing from the silver particles the activation energy needed to create sinter necks in a condensation process on a liquid surface. Nano-disperse, antimicrobial adhesive and coating materials can be manufactured in this way.

The liquid can be a precursor product of the organic component or the organic component. The suggested method is particularly simple to execute. In a single device a homogenous dispersion of the silver particles can be made in the organic component or its precursor product. The adhesive and coating material can be further processed by hardening of the organic component, for example by adding an additional organic component.

For further advantageous embodiments reference is made to the features already described with the antimicrobial adhesive and coating material which features can also be applied appropriately in connection with the method.

Figure 2:
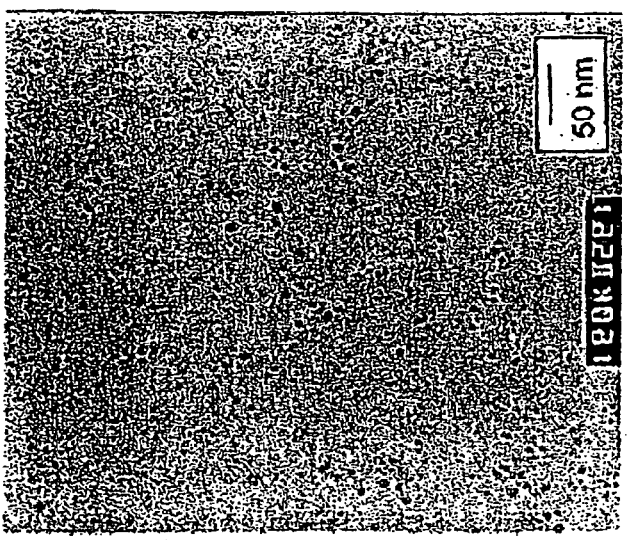
Figure 1:
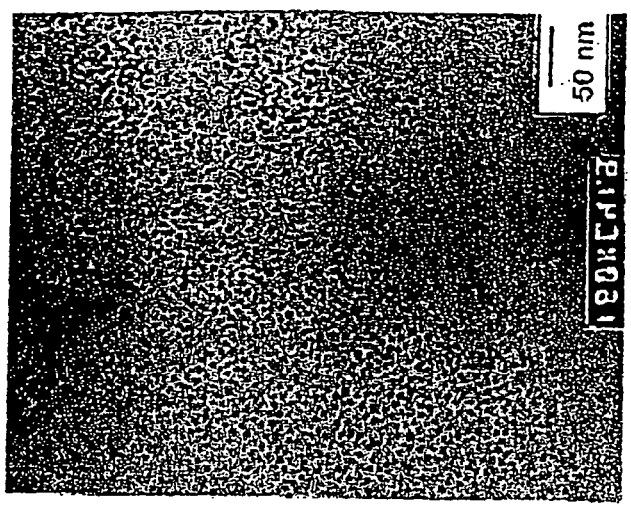
Figure 4:
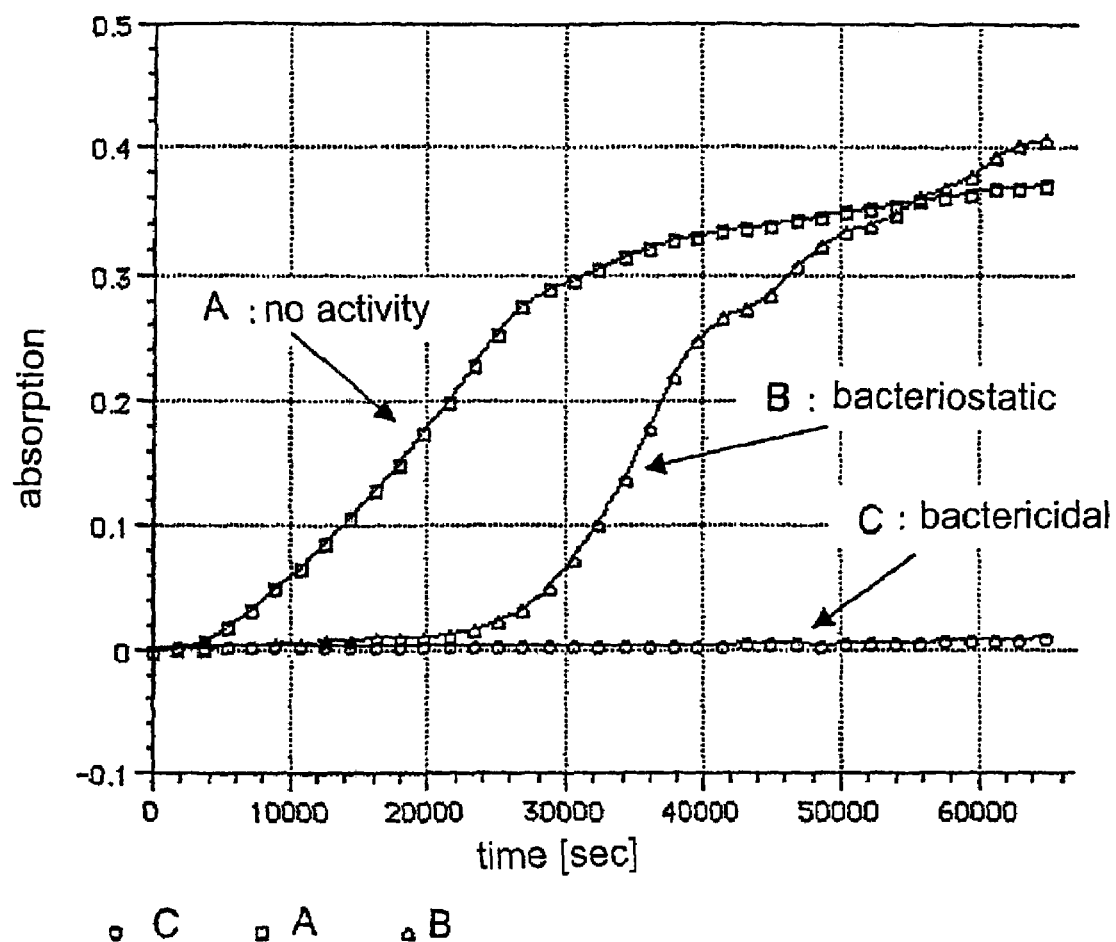
Figure 5:
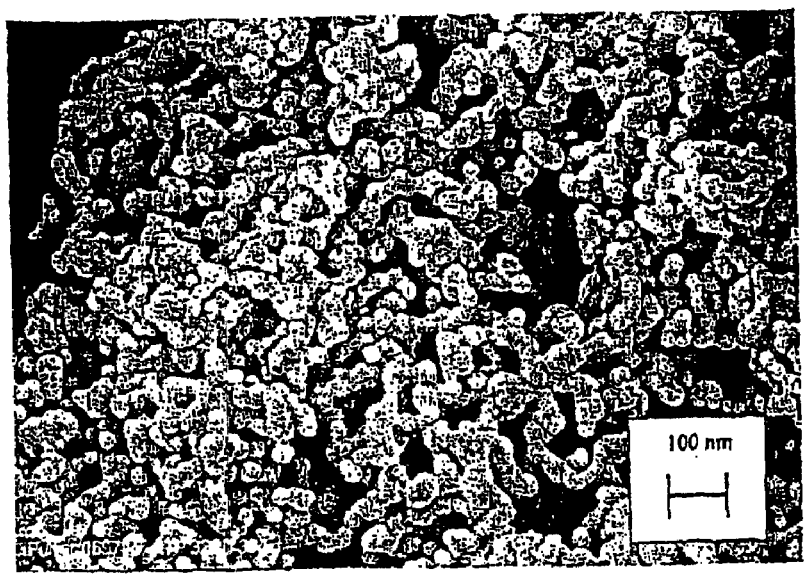
Figure 6:
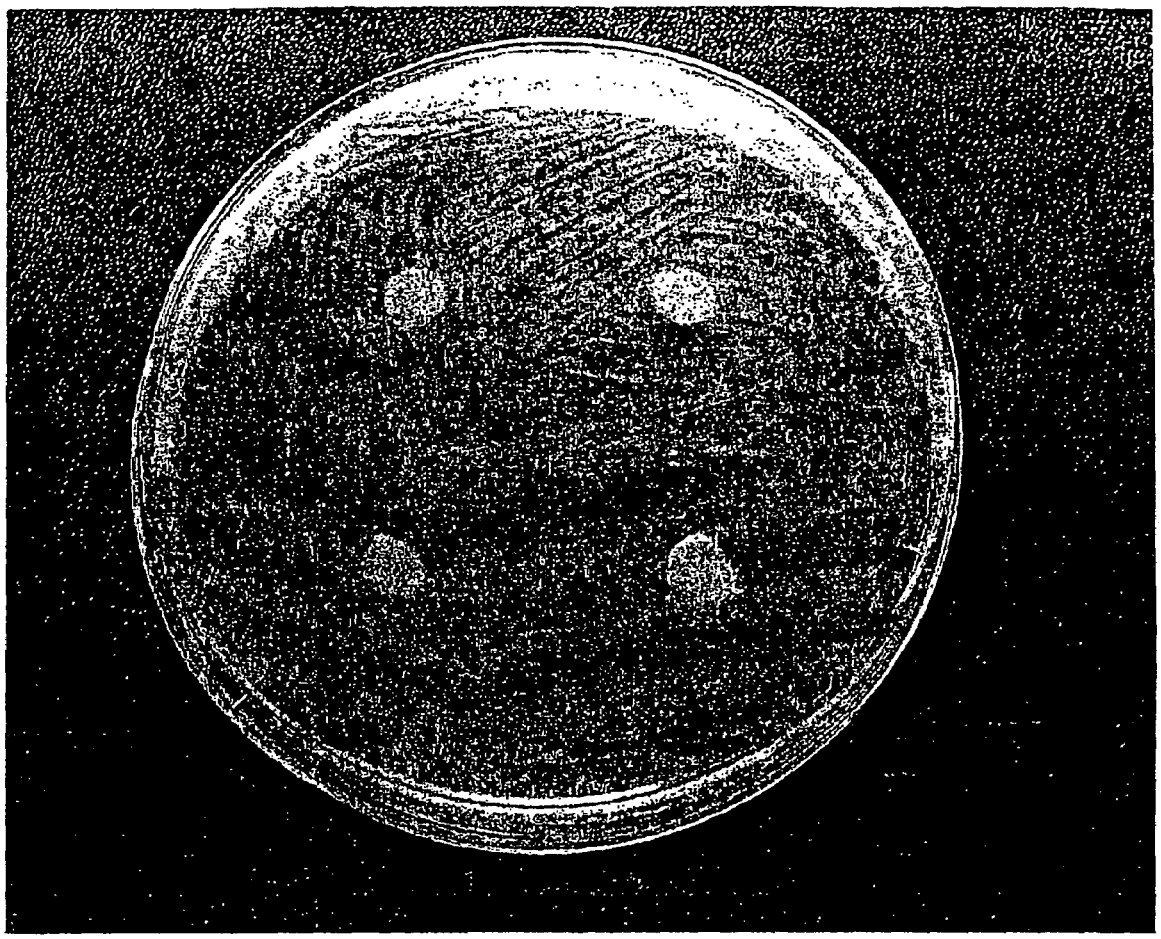

Examples will now be used to describe the invention in more detail based on the drawings. The figures are listed below:

FIG. 1 Silver particles dispersed in polytetrahydrofuran,
FIG. 2 Silver particles dispersed in diethylhexylphthalat,
FIG. 3 Silver particles dispersed in dimethylsiloxan,
FIG. 4 Documentation of the antimicrobial effect of an epoxy resin adhesive containing silver particles,
FIG. 5 A scanning electron microscopic image of a silver aggregate and
FIG. 6 An inhibition zone test of a coating material provided by the invention.

MANUFACTURING OF THE METALLIC SILVER PARTICLES

Silver (99.95 silver wire from the Heraeus company) is vaporized by magnetron sputtering in a vacuum recipient at a temperature of 20° C. and under a pressure of 0.01 to 0.1 mbar in argon atmosphere. Vaporization in the vacuum recipient can also take place thermally, for example, in a crucible. The silver vapor is then precipitated on the surface of a liquid or condensed on a cooled surface together with the vaporized liquid. The liquid can be, for example silicon oil, polytetrahydrofuran, diethylhexylphthalat or dimethylsiloxan. The liquid is continuously stirred so that the precipitated or condensed metallic silver particles are dispersed homogeneously in the liquid. The organic component or a precursor product of the organic component of the adhesive and coating material to be made is preferably used as the liquid.

FIG. 1 shows spherical silver particles dispersed in polytetrahydrofuran in accordance with the aforementioned method. This is a precursor product of an epoxy resin. It can be seen in FIG. 1 that the silver particles have an average grain size of less than 10 nm.

FIG. 2 shows spherical silver particles which have been dispersed in diethylhexylphthalat in accordance with the aforementioned method. This is a component for a coating of polyvinyl chloride (PVC). Also here there is a homogenous dispersion of the silver particles in the component. The silver particles have an average grain size of less than 10 nm.

FIG. 3 shows a dispersion of ball-shaped silver particles in dimethylsiloxan. This is a component of a silicon adhesive. Again the silver particles have an average grain size of less than 10 nm here.

The previously described dispersions can then be hardened, for example, by the addition of a further liquid component. They can also be mixed with functional groups such as acrylate or methacrylate groups, or co-polymerized in case of polytetrahydrofuran for example.

Examples of the manufacturing of antimicrobial adhesive and coating materials are now described.

EXAMPLE 1

Preparation of Bactericidal Silicon Materials:
A component such as a binder of an addition-vulcanizing two-component silicon rubber based on polydimethylphenyl-siloxan (RTV-S691; Wacker) is doped with silver particles made via the method described above. The component is then mixed in the ratio of 9:1 with an additional component such as a hardener. Hardening takes place at T=25° C. The resulting concentration of silver in the hardened material is 0.01 to 5 weight %, preferably 0.05-1 weight % of silver. The hardenable material can be used immediately as adhesive, lacquer or, after addition of suitable pigments or dyes, also as printer's ink.

EXAMPLE 2

Preparation of Bactericidal Epoxy Resin Adhesives:
A hardener (HV 998, Ciba) of a pasty two-component adhesive with an epoxy resin basis (Araldit AV138M, Ciba) is doped with silver nano-particles using the method described above. The doped hardener is mixed into the epoxy resin and hardened at room temperature. The concentration of silver is 0.01 to 5 weight %, preferably 0.1 to 1 weight %, of silver in the hardened two-component adhesive. The hardenable material can be used immediately as adhesive, lacquer or, after addition of suitable pigments or dyes, as printer's ink for example.

EXAMPLE 3

Preparation of Bactericidal and Bacteriostatic Epoxy Resin Adhesives:
Adhesives are prepared on the basis of cationic hardening cycloaliphatic epoxy resins. The epoxy resin ERL 4221 (Union Carbide) is co-polymerized with polytetrahydrofuran (PTHF) with a molecular mass of 1000 (PTHF 1000, BASF). PTHF is used for flexibilization or as plasticizer. The PTHF contains 5 weight % silver incorporated with the method described above (designation: PTHF-VERL-Ag). This results in a silver content of the samples provided by the invention of 1 weight %. No silver is contained in comparable examples. The thermal cationic hardening takes place with the addition of an initiator. For example the iodonium salt Rhodorsil 2074 (Rhodia) can be used as initiator with ascorbic-acid-6-hexadecant (ASHD) as accelerator or with $\alpha,\alpha$-dimethyl-benzylpyridinium hexafluoroantimonat (S. Nakano, T. Endo, J. Polym. Sci.: Part A, 34 (1996) 475). Hardening takes place with the following temperature program: 90 min at 80° C., 60 min at 100° C. and 60 min at 120° C.

The composition of the individual mixtures in weight % and the microbiological effect on *staphylococcus epidermidis* is summarized in the following table.

| Resin | Flexibilisator | Initiator | Type of Example | Microbiological Effect |
| --- | --- | --- | --- | --- |
| 79% ERL 4221 | 20% PTHF | 1% $\alpha,\alpha$-dimethylbenzyl-pyridinium hexafluoro-antimonat | Comparison | None |
| 78% ERL 4221 | 20% PTHF | 1% Rhodorsil 2074, 1% ASHD | Comparison | None; FIG. 4, sample A |
| 79% ERL 4221 | 20% PTHF-VERL-Ag | 1% $\alpha,\alpha$-Dimethylbenzylpyri-dinium hexa-fluororoantimonat | Provided by the invention | Bacteriostatic; FIG. 4, sample B |
| 78% ERL 4221 | 20% PTHF-VERL-Ag | 1% Rhosorsil 2074, 1% ASHD | Provided by the invention | Bactericidal; FIG. 4, sample C |

The results shown in FIG. 4 have been determined in accordance with the method made known from DE 197 51 581 A1. This method is also described in Bechert, Thorsten et al., Nature Medicine, Vol. 6, No. 8 (09/2000). The disclosed contents of the two aforementioned documents are thereby included.

First 8 parallel samples each of the same batch of epoxy resin adhesive are made. The samples usually have a cylindrical shape. They have a length of approximately 1 cm and a diameter of 2 to 5 mm. Then 200 µl of the bacteria-containing solution is filled in each recess of the micro-titer plate. The samples are incubated at 37° C. for one hour. The samples are then removed and washed three times with physiological buffers. Then the samples are placed in the recesses of a micro-titer plate which are filled with a minimal medium. Each recess is filled with 200 µl of minimal medium. The samples are incubated at 37° C. for 24 hours. The samples are then removed and rejected. 50 µl of a full medium (trypcase-soja) are added to each recess of the micro-titer plate. The clouding or absorption of the solution is then measured at 30-minute intervals over a period of 48 hours. The solution is held at a temperature of 37° C. The clouding measurement is made with light of a wave length of 578 nm via a suitable reading device. Cloudiness indicates that bacteria have been released from the surface of the sample to the environment.

The results shown in FIG. 4 indicate that the bactericidal effect of adhesives can be controlled by appropriate selection of the initiator. The hardenable material can be used immediately as adhesive, lacquer or, for example, as printer's ink after addition of suitable pigments or dyes.

FIG. 5 shows a scanning electron microscopic image of the silver aggregate provided by the invention. The silver aggregate essentially consists of ball-shaped primary particles with an average grain size of approximately 20 nm. The primary particles are connected with each other primarily via sinter necks. They form a highly porous framework. The silver aggregate shown here has a size of approximately 10 µm. Such silver aggregates can also be added to the adhesive and coating material instead of the fine silver particles described in the preceding examples. Comparable results are obtained with this with regard to the antimicrobial effect as well as the inhibition zone test.

FIG. 6 shows an inhibition zone test of an adhesive and coating material provided by the invention. This is a polyurethane lacquer to which 0.1 weight % silver particles are added. The silver particles are agglomerates such as those shown in FIG. 5. The samples are placed in TSB-Agar as the culture medium to which *staphylococcus epidermidis* is added as a test organism. The samples were incubated for 48 hours. As FIG. 6 illustrates, the samples do not show an inhibition zone. To this extent they are not viewed as having a cytotoxic effect.

The invention claimed is:

1. Antimicrobial adhesive or coating material which contains as the antimicrobial component metallic silver particles, wherein the silver particles are formed of highly porous aggregates having an average grain size of between 1 µm and 20 µm, the aggregates are formed of primary particles with an average grain size between 10 nm and 150 nm, and the primary particles are connected together by sinter necks, and the silver particles are mixed with a liquid organic component.

2. Antimicrobial adhesive or coating material as defined in claim 1, wherein the organic components are at least partially hardened after mixing in silver particles.

3. Antimicrobial adhesive or coating material as defined in claim 2, wherein the silver particles cooperate with the organic component after the organic component is at least partially hardened to release silver ions in an antimicrobial effective amount that is not cytotoxic.

4. Antimicrobial adhesive or coating material as defined in claim 3, wherein the silver particles are dispersed in the organic component in an amount equal to 0.1% to 5.0% by weight.

5. Antimicrobial adhesive or coating material as defined in claim 4, wherein the primary particles have an average grain size in the range of 80 to 140 nm.

6. Antimicrobial adhesive or coating material as defined in claim 1, wherein the aggregates have an average grain size of 10 µm to 20 µm.

7. Antimicrobial adhesive or coating material as defined in claim 1, wherein the aggregates have a porosity of up to 95%.

8. Antimicrobial adhesive or coating material as defined in claim 4, wherein the aggregates have a surface area of 3 to 6 $m^2$ per gram.

9. Antimicrobial adhesive or coating material as defined in claim 1, wherein the silver has an essentially undisturbed lattice structure.

10. Antimicrobial adhesive or coating material as defined in claim 1, wherein the aggregates have a porosity of up to 95% and a surface area of 3 to 6 $m^2$ per gram.

11. Antimicrobial adhesive or coating material as defined in claim 1, wherein it is made by mixing the organic component with at least one additional organic component.

12. Antimicrobial adhesive or coating material as defined in claim 1, wherein the silver particles are mixed immediately with the liquid organic component or immediately with a liquid precursor product of same.

13. Antimicrobial adhesive or coating material as defined in claim 1, wherein said metallic silver particles are present in an amount of from 0.01 to 5.0 weight %.

14. Antimicrobial adhesive or coating material as defined in claim 1, wherein the aggregates are completely infiltrated with the organic component.

15. Antimicrobial adhesive or coating material as defined in claim 1, wherein the organic component and/or an additional organic component is essentially composed of an acrylate or methacrylate.

16. Antimicrobial adhesive or coating material as defined in claim 1, wherein the organic component and/or an additional organic component is essentially composed of an epoxide, urethane, silicone or cyanoacrylate.

17. Antimicrobial adhesive or coating material as defined in claim 1, including a further constituent comprising a salt or a complex containing cations of at least one of the following metals: Au, Pt, Pd, Ir, Sn, Cu, Sb, Zn.

18. Antimicrobial adhesive or coating material as defined in claim 17, wherein the cations are bound in ion exchangers.

19. Antimicrobial adhesive or coating material as defined in claim 18, wherein the further constituent is a salt of a carboxylic acid.

20. Antimicrobial adhesive or coating material as defined in claim 1, wherein the adhesive or coating material is an adhesive.

21. Antimicrobial adhesive or coating material as defined in claim 1, wherein the organic component and/or an additional organic component contains one or more of the following constituents: solvent, filler material, pigment, binding agent, plasticizer, drying accelerator, fungicide.

22. Antimicrobial adhesive or coating material as defined in claim 1, wherein the adhesive or coating material is a lacquer, a paint or a dispersion which can be hardened.

23. A process of using the antimicrobial adhesive or coating material as defined in claim 1 comprising incorporating the antimicrobial adhesive or coating material in the manufacture and/or coating of wound coverings, bandages, incontinence products, medical devices, packaging materials, for the coating of walls of buildings, housings and/or components of technical devices.

24. Method for the manufacture of an antimicrobial adhesive or coating material as defined in claim 1, with the following steps:
   generating a silver vapor by sputtering or by vaporization in a vacuum recipient,
   condensing the silver vapor and forming silver particles of highly porous aggregates having an average grain size between 1 µm and 20 µm, the aggregates being formed of primary particles with an average grain size between 10 nm and 150 nm, and the primary particles are connected together by sinter necks, and
   mixing the silver particles in an antimicrobial effective amount with a liquid organic component.

25. Method as defined in claim 24, wherein the organic component is at least partially hardened after the mixing in of silver particles.

26. Method as defined in claim 25, wherein the silver particles cooperate with the organic component to release silver ions in an antimicrobial effective amount that is not cytotoxic.

27. Method as defined in claim 24, wherein the silver vapor is condensed during the vapor phase so that the aggregates are created from the primary particles.

28. Method as defined in claim 24, wherein the organic component or a precursor product of same is used as liquid.

29. Method as defined in claim 24, wherein the silver particles are added to a precursor product instead of the organic component and then the organic component is made.

30. Method as defined in claim 24, wherein 0.01 to 5.0 weight % of silver particles are added to the organic component.

31. Method as defined in claim 24, wherein the organic component is mixed with at least one further liquid organic component.

32. Method as defined in claim 24, wherein the organic component and/or the additional organic component are/is essentially composed of an acrylate or a methacrylate.

33. Method as defined in claim 24, wherein the organic component and/or the additional organic component are/is essentially composed of an epoxide, urethane, silicone or cyanoacrylate.

34. Method as defined in claim 24, including the additional step of adding to the organic component and/or the additional organic component a further constituent comprising a salt or a complex containing cations of at least one of the following metals: Au, Pt, Pd, Ir, Sn, Cu, Sb, Zn.

35. Method as defined in claim 34, wherein the cations are bound in ion exchangers and are added at least to the organic component.

36. Method as defined in claim 35, wherein the further constituent is a salt of carboxylic acid.

37. Method as defined in claim 24, wherein one or more of the following is/are added to the organic component and/or the additional organic component: solvent, filler material, pigment, binding agent, plasticizer, drying accelerator, fungicide.

38. Antimicrobial adhesive or coating material as defined in claim 1, wherein the silver particles are dispersed in the organic component in an amount equal to 0.1% to 5.0% by weight, the primary particles have an average grain size in the range of 80 to 140 nm, the aggregates have an average grain size of 10 µm to 20 µm, a porosity between 70% and 95% and a surface area of 3 to 6 $m^2$ per gram.

39. Antimicrobial adhesive or coating material as defined in claim 38, wherein the silver particles cooperate with the organic component after the organic component is at least partially hardened to release silver ions in an antimicrobial effective amount that is not cytotoxic.

\* \* \* \* \*